United States Patent [19]

Kalopissis et al.

[11] 4,226,784

[45] Oct. 7, 1980

[54] 2- AND 5-AMINOALKYLAMINO ANTHRAQUINONE DYES USEFUL AS BASIC DYES IN COLORING HAIR

[75] Inventors: Grégoire Kalopissis, Paris; Andrée Bugaut, Boulogne-sur-Seine, both of France

[73] Assignee: L'Oreal, Paris, France

[21] Appl. No.: 772,227

[22] Filed: Feb. 25, 1977

Related U.S. Application Data

[60] Continuation of Ser. No. 96,645, Dec. 9, 1970, abandoned, which is a division of Ser. No. 607,898, Jan. 9, 1967, Pat. No. 3,617,163.

[30] Foreign Application Priority Data

Jan. 10, 1966 [LU] Luxembourg ............................ 50233
Jun. 24, 1966 [LU] Luxembourg ............................ 51408
Dec. 9, 1966 [LU] Luxembourg ............................ 52555

[51] Int. Cl.$^3$ ........................ A61K 7/13; C07C 97/24; C09B 1/28
[52] U.S. Cl. ...................................... 260/378; 8/404; 260/205; 260/326 A; 260/326 D; 260/326 N; 260/384; 260/556 A; 260/570.5 P; 260/574; 260/575
[58] Field of Search ......................................... 260/378

[56] References Cited

U.S. PATENT DOCUMENTS

| | | | |
|---|---|---|---|
| 2,888,379 | 5/1959 | Bruning et al. | 260/378 |
| 3,232,934 | 2/1966 | Hoare | 260/247.1 |
| 3,442,599 | 5/1969 | Kalopissis et al. | 8/10.1 |
| 3,442,895 | 5/1969 | Bugaut et al. | 260/247.1 |

OTHER PUBLICATIONS

Ciba, Chemical Abstracts, vol. 51, 2032 to 2033 (1957).
Kalopissis et al., Chemical Abstracts, vol. 71, #4127u (1969).
Kalopissis et al., Chemical Abstracts, vol. 71, #92651e (1969).

*Primary Examiner*—Floyd D. Higel
*Attorney, Agent, or Firm*—Cushman, Darby & Cushman

[57] ABSTRACT

A compound of the formula A-NR—$(CH_2)_n$—NHR' wherein R and R' are hydrogen, n is a whole number between 2 and 6 inclusive and A is selected from (1) anthraquinonyl per se wherein NR-$(CH_2)_n$—NHR' is in position 2 or (2) anthraquinonyl of the formula

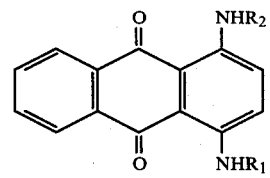

wherein $R_1$ and $R_2$ are selected from hydrogen and lower alkyl, and the NR—$(CH_2)_n$—NHR' chain is in position 5. The compound is useful as a basic dye in coloring the hair.

3 Claims, No Drawings

2- AND 5-AMINOALKYLAMINO ANTHRAQUINONE DYES USEFUL AS BASIC DYES IN COLORING HAIR

This application is a continuation of Ser. No. 96,645, filed Dec. 9, 1970, now abandoned which is a division of Ser. No. 607,898, filed Jan. 9, 1967, now U.S. Pat. No. 3,617,163.

This invention relates to new coloring compositions for dyeing hair.

The object of the present invention is to provide a new article of manufacture consisting of a coloring composition for human hair. This composition is essentially characterized by the fact that it contains, in solution, at least one compound having the following general formula:

$$A-NR-(CH_2)_n-NHR' \qquad (I)$$

in which R and R' may be identical or different and represent a hydrogen atom, a lower alkyl radical or a lower hydroxy-alkyl radical; in which n is a whole number between 2 and 6 inclusive, and in which the radical A represents either:

(1) An anthraquinone radical having the formula:

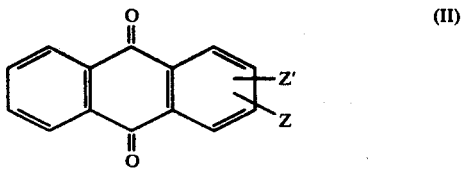

in which case the R in Formula (I) always represents a hydrogen atom, while in Formula (II) Z' represents a hydrogen atom or an $NHR_1$ group, in which $R_1$ may be a hydrogen atom, or a lower alkyl radical, and Z represents a hydrogen atom or an NHR" group, in which R has the significance hereinbefore indicated, and R" is a hydrogen atom, a lower alkyl group or a $-(CH_2)_n-NHR'$ group, in which R' and n have the significances hereinbefore indicated, it being understood that on the anthraquinone ring the $NR-(CH_2)_n-NHR'$ chain specified in formula (I) may occupy only:

(a) Position 1, in which case the Z' radical represents a hydrogen atom, and the Z radical, if it represents anything other than a hydrogen atom, can occupy only positions 4, 5 or 8, or
(b) Position 2, in which case the radicals R', Z and Z' each represent a hydrogen atom, or
(c) Position 5, in which case R' must represent a hydrogen atom, the Z' radical represents an $NHR_1$ group in position 4 and the Z radical represents the $NHR_2$ group in position 1, in which last mentioned group $R_2$ represents a hydrogen atom or a lower alkyl radical and $R_1$ and $R_2$ may be identical or different; or (2) An azo radical having the formula:

$$B_1-N=N-B_2 \qquad (III)$$

in which $B_1$ and $B_2$ each represent an aromatic or heterocyclic group which may or may not be substituted by one or more nitro, halogen, alkyl, hydroxy, or aminoacyl groups; or (3) A benzene ring having the following formula:

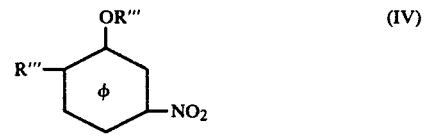

in which R''' represents a hydrogen atom or a lower alkyl radical with the $NR-(CH_2)_n-NHR'$ chain in para position with respect to the alkoxy group and in which R represents a hydrogen atom and R' has the significance hereinbefore indicated.

The dyes of formula (I) have several advantages; for example, their great affinity for keratinic fibers makes colors thus obtained very resistant to shampooing. Moreover, these dyes provide a great range of shades, running from yellow to blue, which are not adversely affected by light over long periods of time.

In addition, the dyes used to prepare the coloring compositions according to the invention have the advantage of being soluble in water for a pH range of from 4 to 10. To adjust the pH, an organic or mineral acid such as lactic acid or hydrochloric acid may be used.

The period during which the aforesaid coloring solutions are in contact with the hair may vary greatly, preferably from 5 to 30 minutes. The temperature at which these coloring solutions are applied may also be varied but in most cases they may be used at ordinary temperatures. The concentration of dyes of formula (I) in the coloring compositions may also be varied, but this concentration should preferably be between 0.01% and 3%.

The new dyes may be mixed with each other or with other dyes usually employed for dyeing hair.

Moreover, the coloring compositions according to the invention may contain such generally used ingredients as dispersing or wetting agents, thickeners, detergents, softeners, and perfumes.

Among the compounds described above as serving as active products for coloring compositions according to the invention are certain new chemical compounds. Therefore another object of the present invention is to provide, as new articles of manufacture, the new chemical compounds having the following general formula:

$$A-NR-(CH_2)_n-NHR' \qquad (I)$$

in which R and R' may be identical or different and represent a hydrogen atom, a lower alkyl radical or a lower hydroxy-alkyl radical; in which n is a whole number between 2 and 6 inclusive; in which the radical A represents either:

(1) A non-substituted anthraquinone radical in which case the $NR-(CH_2)_n-NHR'$ chain is in position 2, R and R' representing hydrogen atoms; or (2) An anthraquinone radical having the formula:

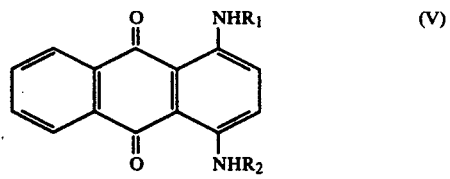

in which $R_1$ and $R_2$ may be identical or different and represent a' hydrogen atom, or a lower alkyl radical, it being understood that on the anthraquinone ring, the NR—(CH$_2$)$_n$—NHR' chain specified in formula (I), may occupy only position 5, with R and R' necessarily representing a hydrogen atom; or (3) a paranitro-phenylazo phenyl responding to the formula:

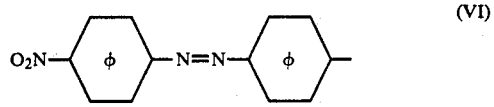

(VI)

it being understood that the chain —NR—(CH$_2$)$_n$—NHR' which appears in general formula I is attached in position 4, while position 4' is occupied by the nitro group.

Another object of the present invention is to provide a process for dyeing keratinic fibers, which is essentially characterized by the fact that the fibers to be treated, particularly hair, are impregnated with a coloring composition according to the invention. This composition is left on for 5 to 30 minutes; then the hair is rinsed and dried.

The compounds of formula (I) in which the radical A represents a radical having the above-indicated formula (II) with an NM—(CH$_2$)$_n$—NHR' chain in position 1, may be prepared in the usual manner, by condensing a diamine responding to the formula NH$_2$—(CH$_2$)$_n$—NHR' on an anthraquinone derivative which is α-monohalogenated or dihalogenated in position 1, 5 or 1, 8, or even on quinizarine.

Those compounds according to formula (I) in which the radical A represents a radical responding to Formula (II) and which comprise a NH—(CH$_2$)$_n$—NH$_2$ chain in position 2 may be prepared, in a known manner, from 2-amino anthraquinone by reacting an E,ω-dihalogene-alkane with an alkaline derivative of an 2-arylsulfonyl-amino anthraquinone, then condensing the resulting halogenated derivative on potassium phthalimide and finally hydrolyzing the resulting phthalimide derivative, first with sulfuric acid and then with hydrazine hydrate.

Those compounds according to Formula (I) in which the radical A represents a radical responding to Formula (II) and which comprise a NH—(CH$_2$)$_n$—NH$_2$ chain in position 5 may be prepared, in a known manner, by condensing a diamine responding to the formula NH$_2$—(CH$_2$)$_n$—NH$_2$ on 1,4-diamino-5-nitro anthraquinone.

Compounds responding to formula (I), in which the radical A represents a radical responding to the above-indicated formula (III), may be obtained in the usual manner by combining the diazonium salt of the amine B$_1$—NH$_2$ with the amine B$_2$—NR—(CH$_2$)$_n$—NHR'.

Compounds responding to formula (I) in which the radical A represents a radical responding to the above-indicated formula (IV) may be obtained in the usual manner from amines responding to the formula:

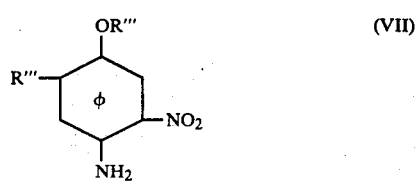

(VII)

by bonding a —(CH$_2$)$_n$—NHR' group to the NH$_2$ group of the aromatic ring.

In order that the invention may be better understood, several examples of the preparation and use of the dyes according to Formula (I) will now be described, purely by way of illustration without limiting the scope of the invention to the details thereof.

EXAMPLE I

Preparation of 4-methylamino-1-(β-aminoethyl)-amino anthraquinone

The reaction used in preparing this compound may be diagrammatically represented in the following manner:

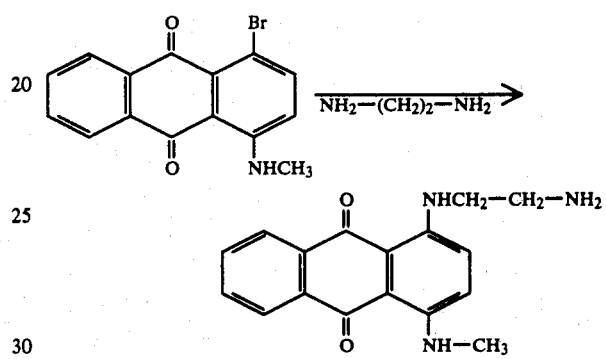

A toluenic solution of 4-methylamino-1-bromo anthraquinone is heated to reflux for several hours with an excess of ethylenediamine. After cooling, the toluenic solution is treated several times with a solution of normal hydrochloric acid. The hydrochloric extracts are collected, and then rendered alkaline in order to liberate the desired base, which is extracted by means of ethyl acetate. Oxalic acid is added to this ethyl acetate solution and the desired amine is precipitated in the form of oxalate which is then dried.

The corresponding base is liberated by rendering the solution alkaline and is isolated in the usual manner. It melts at 168° C. after being crystallized in toluene.

4-methylamino-1-(β-acetylaminoethyl)-aminoanthraquinone is prepared from this base by adding acetic anhydride to a solution of 4-methylamino-1-(β-aminoethyl)-amino-anthraquinone in ethyl acetate. This monoacetate, recrystallized in normal propyl alcohol melts at 220° C. Analysis yields the following results:

| Analysis | Calculated for $C_{19}H_{19}N_3O_3$ | Found |
|---|---|---|
| C % | 67.65 | 67.50–67.44 |
| H % | 5.64 | 5.86–5.84 |
| N % | 12.46 | 12.20–12.22 |

EXAMPLE II

Preparation of 4-methylamino-1-(γ-aminopropyl)-amino anthraquinone

The reaction used to prepare this compound may be diagrammatically represented in the following manner:

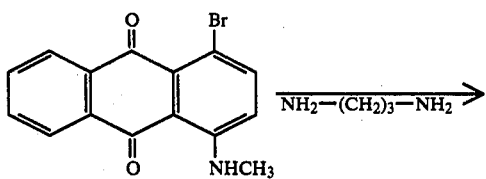

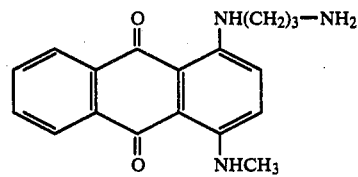

A solution of 4-methylamino-1-bromo anthraquinone in a solvent such as toluene is heated to reflux for several hours with an excess of 1,3-diamino propane. After the reaction mixture has been treated in a manner similar to that described in Example I, the 4-methylamino-1-(γ-aminopropyl)—amino anthraquinone is isolated and after being crystallized in toluene, melts at 142° C.

The calculated molecular weight of this compound is 309. The molecular weight found experimentally by potentiometric determination is 303.

The monoacetate obtained from this base melts at 224° C.

EXAMPLE III

Preparation of 1-(γ-aminopropyl)-amino anthraquinone

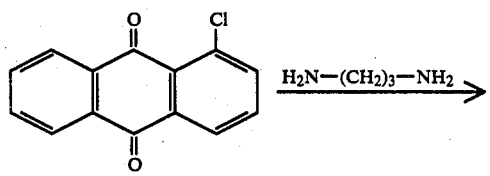

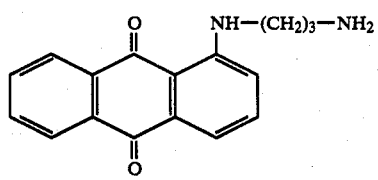

A solution of 1-chloro anthraquinone in a solvent such as toluene is heated to reflux for several hours with an excess of 1,3-diamino propane. After cooling, the toluenic solution is treated several times with a solution of normal hydrochloric acid. The hydrochloric extracts are collected, and then rendered alkaline in order to liberate the desired base, which crystallizes. After drying and recrystallization in toluene, it melts at 152° C.

1-(γ-acetylaminopropyl)—amino anthraquinone is obtained from this base by adding acetic anhydride to a solution of 1-(γ-aminopropyl)—amino anthraquinone in ethyl acetate. This monoacetate recrystallized in ethyl alcohol, melts at 202° C. Analysis yields the following results:

| Analysis | Calculated for $C_{19}H_{18}N_2O_3$ | Found |
|---|---|---|
| C % | 70.81 | 70.73–70.70 |
| H % | 5.59 | 5.61–5.62 |

| Analysis | Calculated for $C_{19}H_{18}N_2O_3$ | Found |
|---|---|---|
| N % | 8.69 | 8.54–8.45 |

EXAMPLE IV

Preparation of 1-(β-aminoethyl)-amino-2-nitro-4-methoxy benzene

The process used to synthesize this compound may be diagrammatically represented in the following manner:

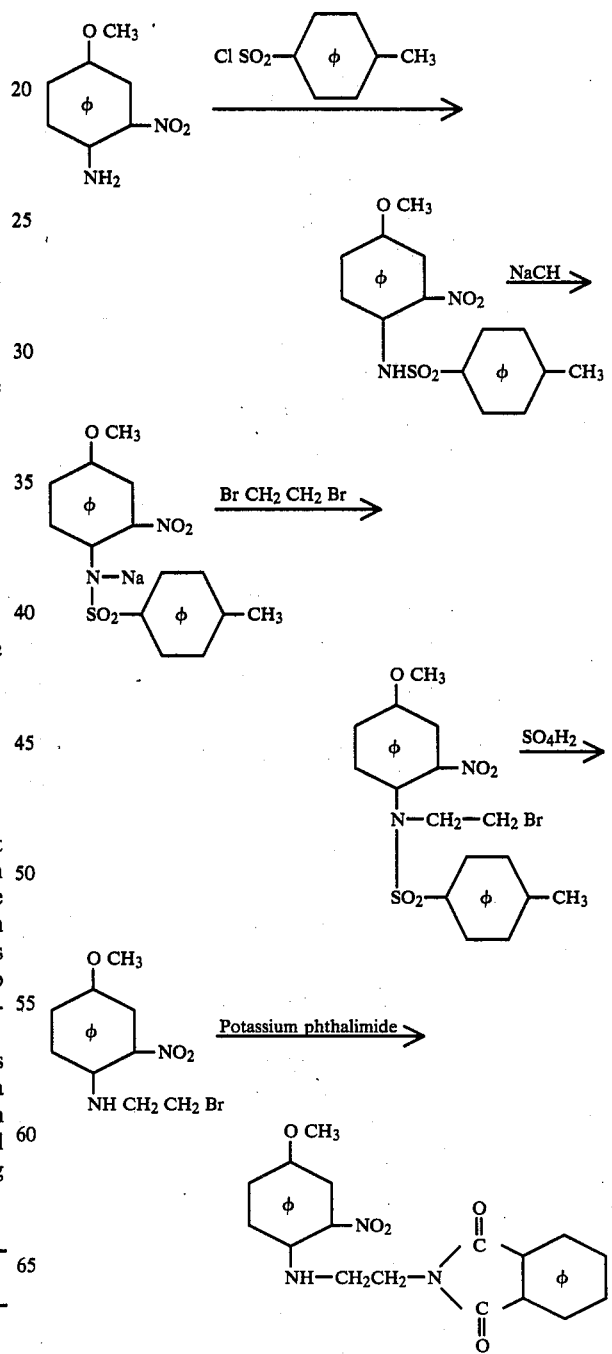

-continued

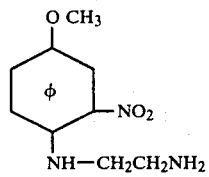

It may be noted that the brominated derivative obtained at the end of the fourth step in this method of preparation is obtained by following the process described in Luxembourg patent application No. 49,213, filed on 30 July 1965. Nevertheless, details of all the steps in this synthesis process will be given below.

Step 1: Preparation of
1-N-p-toluene-sulfonylamino-2-nitro-4-methoxy benzene 0.12 mol (22.86 g) of p-toluene sulfochloride is added slowly at 30° C. with constant stirring to a solution of 0.1 mol (16.8 g) of 1-amino-2-nitro-4-methoxy benzene in 60 cm³ of pyridine. When the addition is complete, the reaction mixture is kept at the ambient temperature for 6 hours. Then it is poured over 300 g of ice to which 30 cm³ of hydrochloric acid have been added, and dried. The crude product is redissolved in a ½ N sodium hydroxide solution. The obtained solution is filtered, then neutralized with hydrochloric acid. (4 g of the initial product are recovered being insoluble in the sodium hydroxide) 25 g of 1-N-p-toluenesulfonylamino-2-nitro-4-methoxy benzene are dried and, after recrystallization in alcohol, melt at 102° C. Analysis of the product yields the following results:

| Analysis | Calculated for $C_{14}H_{14}O_5N_2S$ | Found |
|---|---|---|
| C % | 52.17 | 52.09–52.28 |
| H % | 4.34 | 4.43–4.44 |
| N % | 8.69 | 8.74–8.92 |

Step 2: Preparation of the sodium derivative of
1-N-p-toluenesulfonylamino-2-nitro-4-methoxy benzene 0.155 mol of 1-N-p-toluenesulfonylamino-2-nitro-4-methoxy benzene is dissolved in 600 cm³ of ½ N soda, then 250 cm³ of 10 N sodium hydroxide are added to this solution with constant stirring. Drying yields 48 g of the sodium derivative which are washed first with a little alcohol, then with a little acetone.

Step 3: Preparation of
1-(N-p-toluenesulfonyl)-N-β-bromoethyl) amino-2-nitro-4-methoxy benzene 0.0103 mol (3.56 g) of the sodium derivative of 1-N-p-toluenesulfonylamino-2-nitro-4-methoxy benzene is dissolved in 5 cm³ of dimethylformamide. 0.023 mol (2 cm³) of 1,2-dibromo ethane is added and the mixture is heated to reflux for 15 minutes and is then poured into 50 cm³ of water. After extraction with ethyl acetate, the ethyl acetate solution is washed with ½ N sodium hydroxide to eliminate a little of the 1-N-p-toluene-sulfonylamino-2-nitro-4-methoxy benzene. It is then washed with water. Concentration then yields about 10 cm³ to which a little hexane is added. Drying yields 2.7 g of 1-(N-p-toluenesulfonyl-N-β-bromoethyl)-amino-2-nitro-4-methoxy benzene, which, after recrystallization in absolute alcohol, melts at 117° C. Analysis yields the following results:

| Analysis | Calculated for $C_{16}H_{17}N_2O_5S\ Br$ | Found |
|---|---|---|
| C % | 44.75 | 44.79–44.94 |
| H % | 3.96 | 4.17–4.14 |
| N % | 6.52 | 6.73–6.61 |

Step 4: Preparation of
1-N-β-bromoethylamino-2-nitro-4-methoxy benzene 0.093 mol (40 g) of 1-(N-p-toluenesulfonyl-N-β-bromoethyl) amino-2-nitro-4-methoxy benzene is dissolved in 160 cm³ of concentrated sulfuric acid, the temperature being held between 0° and 5° C. The reaction mixture is left at 0° C. for 3 hours. Then it is poured over 1.2 kg of crushed ice. Drying yields 25.1 g of 1-N-β-bromoethylamino-2-nitro-4-methoxy benzene which, after recrystallization in a mixture of benzene and hexane, melts at 57° C. Analysis yields the following results:

| Analysis | Calculated for $C_9H_{11}N_3O_3Br$ | Found |
|---|---|---|
| C % | 39.27 | 39.41–39.36 |
| H % | 4.00 | 4.18–4.20 |
| N % | 10.18 | 10.39–10.27 |

Step 5: Preparation of
1-N-β-phthalimidecethylamino-2-nitro-4-methoxy benzene 0.27 mol (74 g) of 1-N-β-bromoethylamino-2-nitro-4-methoxy benzene is dissolved in 290 cm³ of dimethylformamide. 0.32 mol (59.5 g) of potassium phthalimide is added and the reaction mixture is heated to reflux for an hour. It is filtered while boiling, then the filtrate is cooled. Drying yields 79 g of 1-N-β-phthalimidoethylamino-2-nitro-4-methoxy benzene which, after recrystallization in dioxane, melts at 212° C. Analysis of the product yields the following results:

| Analysis | Calculated for $C_{17}H_{15}N_3O_5$ | Found |
|---|---|---|
| C % | 59.82 | 59.61–59.73 |
| H % | 4.39 | 4.42–4.60 |
| N % | 12.31 | 12.50–12.48 |

Step 6: Preparation of
1-N-β-aminoethylamino-2-nitro-4-methoxy benzene 0.1 mol (34.1 g) of 1-N-β-phthalimidoethyl-amino-2-nitro-4-methoxy benzene in solution in 350 cm³ of propanol is heated to reflux for an hour with 0.2 mol (10.2 g) of hydrazine hydrate. The reaction mixture is boiled dry to eliminate the phthalhydrazide formed. After the filtrate has been cooled, the small amount of unreacted initial product is recovered by filtration. The propanolic solution is then saturated with gaseous hydrochloric acid and drying yields 22.5 g of the desired product in the form of a hydrochloride. This hydrochloride after recrystallization in water, when analyzed, yields the following results:

| Analysis | Calculated for C₉H₁₄N₃O₃Cl | Found |
|---|---|---|
| C % | 43.63 | 43.79–43.80 |
| H % | 5.65 | 5.65–5.70 |
| N % | 16.96 | 17.05–17.08 |

The 1-N-β-aminoethylamino-2-nitro-4-methoxy benzene isolated from this monohydrochloride in the usual manner melts at 57° C.

EXAMPLE V

Preparation of 1,4-diamino-5-γ-aminopropylamino anthraquinone

The reaction used to prepare this compound may be diagrammatically represented in the following manner:

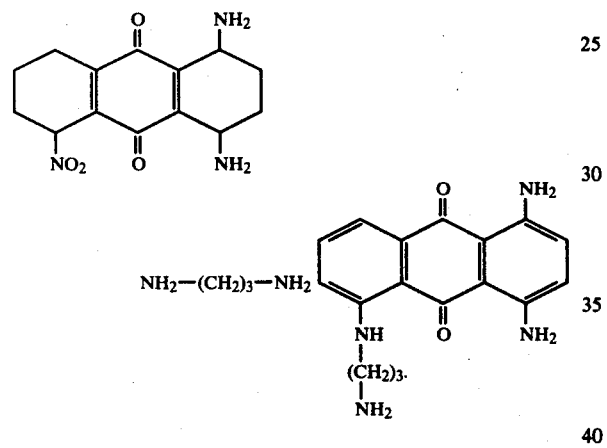

0.4 mol (113.2 g) of 1,4-diamino-5-nitro anthraquinone is heated at 90° for 4 hours in 6 mols (444 g) of 1,3-diaminopropane.

The reaction mixture is poured into 2 liters of cold water. Drying yields 109 g of a crude product which is washed very carefully with water.

After two recrystallizations in propanol 72 g of 1,4-diamino-5-γ-aminopropylamino anthraquinone are obtained, which melt at 165° C.

Analysis of the product yields the following results:

| Analysis | Calculated for C₁₇H₁₈O₂N₄ | Found |
|---|---|---|
| C % | 65.80 | 65.83–65.61 |
| H % | 5.80 | 5.95–6.03 |
| N % | 18.03 | 17.78–17.90 |

Example VI

Preparation of azo [(para-nitraniline)→(N-ethyl-N-β-aminoethyl anilino)]

0.2 mol (27.6 g) of para-nitraniline is diazotized in the conventional manner in a hydrochloric medium. A solution of 0.2 mol (32.8 g) of N-ethyl-N-β-aminoethylaniline in 30 cm³ of acetic acid is added drop by drop, while maintaining the temperature at about 5° C., to the hydrochloric solution of diazonium salt thus obtained.

Drying yields 72 g of this azo compound in the form of a monohydrochloride.

This hydrochloride is dissolved in boiling water and rendered alkaline. Drying yields 56.58 g of the azo compound which, after recrystallization in alcohol and then in benzene, melts at 134° C.

Analysis of the product yields the following results:

| Analysis | Calculated for C₁₆H₁₉N₅O₂ | Found |
|---|---|---|
| C % | 61.34 | 61.35–61.30 |
| H % | 6.07 | 6.14–6.20 |
| N % | 22.36 | 22.44–22.29 |

EXAMPLE VII

Preparation of 2-β-amine-ethylamino anthraquinone

The preparation process may be diagrammatically represented in the following manner:

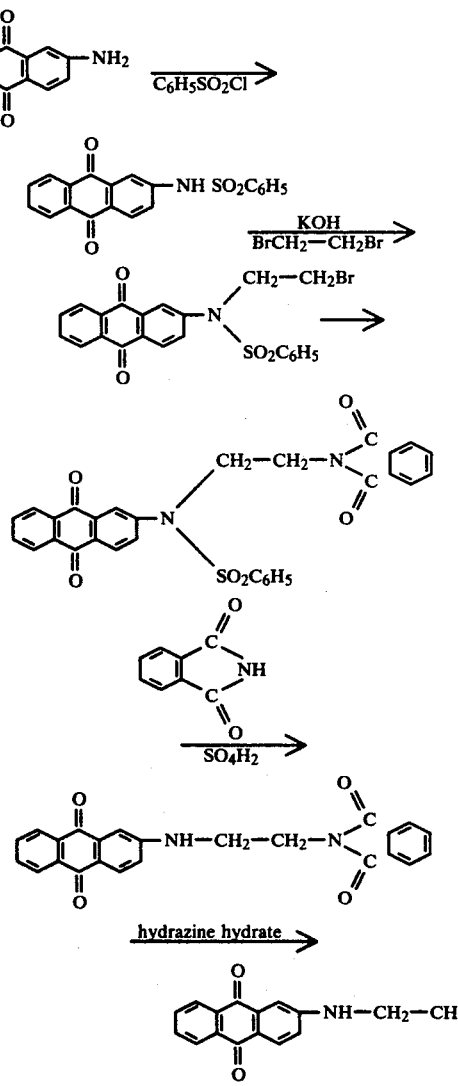

Step 1: Preparation of 2-N-benzenesulfonyl—amine anthraquinone 1.32 mol (166 cm³) of benzenesulfochloride is added little by little at 45° C. with constant stirring to a solution of 1 mol (223 g) of 2-amino anthraquinone in 1800 cm³ of pyridine. When the addition is complete the reaction mixture is kept at 45° C. for 4 hours. It is then cooled to 0° C. Drying yields the crude product which is then washed successively in slightly hydrochloric water, in water, and in alcohol. 320 g of practically pure benzene-sulfonamide are thus obtained, which melt at 276° C. 12 g of slightly less pure benzene-sulfonamide may be recovered from the pyridine filtrate by dilution.

Step 2: Preparation of 2-(N-benzenesulfonyl-N-8-bromoethyl—amino anthraquinone 0.05 mol (18.15 g) of 2-N-benzenesulfonyl—amino-anthraquinone is dissolved in 90 cm³ of dimethyl formamide at 60° C. 3.08 g of potassium hydroxide in solution in 2 cm³ of water and 6 cm³ of alcohol are added, and then, as rapidly as possible, 0.1 mol (18.8 g) of 1,2-dibromo ethane. After the reaction mixture has been kept in a boiling water-bath for two hours, it is poured into a liter of ice water. Drying yields the crude product, which is treated with a ½ N sodium hydroxide solution to eliminate a little unreacted 2-N-benzenesulfonyl—amino anthraquinone. The product is then washed with water. 15 g of 2-(N-benzenesulfonyl-N-$\beta$-bromoethyl)—amino-anthraquinone are thus obtained which, after recrystallization in acetic acid, melt at 155° C.

Step 3: Preparation of 2-(N-benzenesulfonyl-N-$\beta$-phthalimidoethyl)amino anthraquinone 0.317 mol (148 g) of 2-(N-benzenesulfonyl-N-$\beta$-bromoethyl)amino anthraquinone is dissolved in 675 cm³ of dimethylformamide; then 0.412 mol (76.5 g) of potassium phthalimide is added. The reaction mixture is carried to reflux for an hour, then cooled. Next it is poured into 6 liters of ice water. Drying yields 138 g of a crude product which, after recrystallization in acetic acid, melts at 236° C.

Analysis of the product yields the following results:

| Analysis | Calculated for $C_{30}H_{20}N_2O_6S$ | Found |
| --- | --- | --- |
| C % | 67.16 | 67.07–66.93 |
| H % | 3.73 | 3.87–3.80 |
| N % | 5.22 | 5.27–5.20 |

Step 4: Preparation of 2-N-$\beta$-phthalimidoethylamino anthraquinone 0.225 mol (121 g) of 2-(N-benzenesulfonyl-N-$\beta$-phthalimidoethyl)-amino anthraquinone is dissolved in 600 cm³ of concentrated sulfuric acid while maintaining the temperature between 25° and 30° C. The reaction mixture is left at the ambient temperature for 5 hours; then it is poured over 5 kg of crushed ice. Drying yields 87 g of 2-N-$\beta$-phthalimidoethyl-amino anthraquinone, which melts at 270° C.

Step 5: Preparation of 2-$\beta$-aminoethylamino anthraquinone 0.21 mol (83 g) of 2-N-$\beta$-phthalimidoethylamino anthraquinone in solution in 300 cm³ of diethyleneglycol is heated at 110° C. for 2 hours with 0.42 mol (21.5 g) of 98% hydrazine hydrate. After cooling, the reaction mixture is poured into 1.500 liters of water. It is acidified by adding concentrated hydrochloric acid while stirring and is put in a boiling water-bath until the resultant hydrochloride dissolves. After cooling, drying yields 59 g of the hydrochloride of 2-N-$\beta$-aminoethylamino anthraquinone containing a little phthalhydrazide hydrochloride. This crude product is treated with 350 cm³ of a 2-N potassium hydroxide solution. Drying yields 45 g of practically pure 2-N-$\beta$-aminoethylamino anthraquinone which, after recrystallization in pyridine, melts at 180° C.

Analysis of the product yields the following results:

| Analysis | Calculated for $C_{16}H_{14}N_4O_2$ | Found |
| --- | --- | --- |
| C % | 72.18 | 72.43–72.35 |
| H % | 5.26 | 5.42–5.35 |
| N % | 10.52 | 10.54–10.40 |

EXAMPLE VIII

The following hair coloring composition is prepared:

| | |
| --- | --- |
| 1-($\beta$-aminoethyl)-amino-2-nitro-4-methoxy benzene | 0.21 g |
| Lauric alcohol oxyethylenated with 10.5 mols of ethylene oxide | 1.00 g |
| 10% citric acid solution, q.s.p. | ph = 9 |
| Water, q.s.p. | 100 cm³ |

This composition is applied to "deep blonde" hair and left for 10 minutes. The hair is then rinsed and shampooed. A "deep copper mahogany" shade is obtained.

EXAMPLE IX

The following coloring composition is prepared:

| | |
| --- | --- |
| 4-methylamino-1-($\gamma$-aminopropyl)-amino anthraquinone | 0.25 g |
| lauric alcohol oxyethylenated with 10.5 mols of ethylene oxide | 5.00 g |
| 10% citric acid solution, q.s.p. | pH = 7 |
| Water, q.s.p. | 100 cm³ |

This composition is applied to brown hair with light "auburn" glints and left for 10 minutes. The hair is then rinsed and shampooed. A "blue black" shape is obtained.

EXAMPLE X

The following coloring composition is prepared:

| | |
| --- | --- |
| 4-methylamino-1-($\gamma$-aminopropyl)-amino anthraquinone | 0.05 g |
| 1-amino-2-nitro-4-methylamino benzene | 0.17 g |
| 1-amino-3-nitro-6-($\gamma$-N-N-diethylaminopropyl)-amino benzene | 0.11 g |
| lauric alcohol oxyethylenated with 10.5 mols. of ethylene oxide | 3.00 g |
| ½ N sodium carbonate solution, q.s.p. | pH = 9.5 |

| | |
|---|---|
| water, q.s.p. | 100 cm³ |

This composition is applied to 100% white hair and left for 10 minutes. The hair is then rinsed and shampooed. A "deep ash blonde" shade is obtained.

EXAMPLE IX

The following coloring composition is prepared:

| | |
|---|---|
| 4-methylamino-1-(γ-aminopropyl)-amino anthraquinone | 0.12 g |
| (γ-aminopropyl)-amino anthraquinone | 0.33 g |
| 1-amino-2-methyl-4-nitro-5-(β-aminoethyl)-amino benzene | 0.07 g |
| lauric alcohol oxyethylenated with 10.5 mols of ethylene oxide | 3.5 g |
| ½ N sodium carbonate solution, q.s.p. | pH = 9 |
| water, q.s.p. | 100 cm³ |

This composition is applied to 100% white hair and left for 10 minutes. The hair is then rinsed and shampooed. A "strong steel grey" shade is obtained.

EXAMPLE XII

The following coloring composition is prepared:

| | |
|---|---|
| 1,4-diamino-5-γ-aminopropylamino anthraquinone | 0.13 g |
| lauric alcohol oxyethylenated with 10.5 mols of ethylene oxide | 5 g |
| water, q.s.p. | 100 g |

The pH of this composition is 9.5. It is applied to bright chestnut hair with golden glints and left for 10 minutes. The hair is then rinsed and shampooed.

This yields a chestnut shade with ashy glints.

EXAMPLE XIII

The following coloring composition is prepared:

| | |
|---|---|
| 1,4-diamino-5-γ-aminopropylamino anthraquinone | 0.060 g |
| 1-γ-aminopropylamino anthraquinone | 0.075 g |
| 4-nitro-3-β-aminoethylamino-N,N-dimethylaniline | 0.015 g |
| lauric alcohol oxyethylenated with 10.5 mols of ethylene oxide | 5 g |
| 20% citric acid solution q.s.p. | pH = 7 |
| water, q.s.p. | 100 g |

This composition is applied to 90% white hair and left for 10 minutes. The hair is then rinsed and shampooed.

This yields a strong grey with light mauve overtones.

EXAMPLE XIV

The following coloring composition is prepared:

| | |
|---|---|
| monoazo[(φ-nitraniline)→(N-ethyl-N-β-aminoethyl-aniline)] | 0.5 g |
| n-butyl ether of ethyleneglycol | 25 g |
| β-naphthol oxyethylenated wtih 6.4 mol. of ethylene oxide | 12.5 g |
| water, q.s.p. | 100 g |

This solution is applied to natural grey hair in the ratio of 1 volume of solution to an equivalent weight of hair. It is left for 30 minutes at the ambient temperature.

After rinsing, shampooing and drying, a moderate red-orange shade is obtained.

EXAMPLE XV

The following solution A is prepared:

| | |
|---|---|
| 1,4-diamino-5-N(γ-aminopropyl)-amino anthraquinone | 2 g |
| monoazo[(p-nitraniline)→(N-ethyl-N-β-amino-ethyl aniline)] | 2 g |
| n-butyl monoether of ethylene glycol, q.s.p. | 100 g |

The coloring composition is obtained by diluting solution A in the ratio of:

1 volume of β-naphthol oxyethylenated with 6.4 mols of ethylene oxide;

5 volumes of water;

2 volumes of solution A.

The composition thus prepared is applied to natural grey hair in the ratio of 1 volume of solution to an equivalent weight of hair and left for 30 minutes at the ambient temperature.

After rinsing, shampooing and drying, a purple grey shade is obtained.

EXAMPLE XVI

| | |
|---|---|
| 2-β-aminoethylamino anthraquinone | 0.1 g |
| iso-octyl-phenyl-polyethoxy-ethanol | 5 g |
| 2-butoxy ethanol | 6 g |
| 1 N Na₂CO₃ solution, q.s.p. | pH = 8 |
| water, q.s.p. | 100 g |

This composition is applied to 90% white hair and left for 20 minutes. The hair is then rinsed and shampooed.

This yields a mahogany blonde shade.

EXAMPLE XVII

The following setting nd coloring lotion is prepared:

| | |
|---|---|
| poly-vinyl pyrrolidone | 2 g |
| 1-γ-aminopropylamino anthraquinone | 0.020 g |
| 1,4-diamino-5-γ-aminopropylamino anthraquinone | 0.028 g |
| 2-β-aminoethylamino anthraquinone | 0.036 g |
| ethyl alcohol at 96° | 50 cm³ |
| water, q.s.p. | 100 cm³ |

The pH of this solution is adjusted to 7 with a normal solution of sodium carbonate.

This lotion is applied before the set without rinsing and the hair is arranged as usual before drying.

70% white hair turns a strong violet grey while setting.

It will be understood that the foregoing examples have been given purely by way of illustration and that other specific preparations falling within the scope of the general formula given in the summary may be used without thereby departing from the basic principles of the invention.

What is claimed is:

1. A compound of the formula

A—NR—(CH₂)ₙ—NHR' wherein R and R' are hydrogen, n is a whole number between 2 and 6 inclusive and A is selected from the group consisting of (1) anthraquinonyl per se in which case the NR—(CH$_2$)$_n$—NHR' chain is in position 2 of said anthraquinonyl or (2) anthraquinonyl of the formula

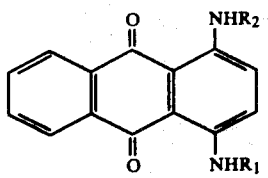

wherein R$_1$ and R$_2$ are selected from the group consisting of hydrogen and lower alkyl and the NR—(CH$_2$)$_n$—NHR' chain occupies position 5 of said anthraquinonyl.

2. The compound of claim 1 which is 2-β-aminoethylamino anthraquinone.

3. 1,4-diamino-5-γ-aminopropylamino anthraquinone.

* * * * *